United States Patent [19]

Lee

[11] 4,276,229

[45] Jun. 30, 1981

[54] PROCESS FOR PREPARING CARBAMATE COMPOUNDS

[75] Inventor: Young-Jin Lee, South Charleston, W. Va.

[73] Assignee: Union Carbide Corporation, New York, N.Y.

[21] Appl. No.: 133,789

[22] Filed: Mar. 25, 1980

[51] Int. Cl.$^3$ .................. C07C 119/06; C07C 131/00
[52] U.S. Cl. ........................... 260/453 RW; 564/255; 560/134
[58] Field of Search ................ 260/453 RW, 566 AC; 560/134; 564/255

[56] References Cited

U.S. PATENT DOCUMENTS 3,847,988  11/1974  Gold .............................. 260/453 RW

*Primary Examiner*—Henry R. Jiles
*Assistant Examiner*—Robert C. Whittenbaugh
*Attorney, Agent, or Firm*—Dale Lynn Carlson

[57] ABSTRACT

This invention relates to an improved process for preparing carbamate compounds by reacting an active hydrogen-containing compound with an N-alkylcarbamoyl sulfonate salt in the presence of a base.

8 Claims, No Drawings

PROCESS FOR PREPARING CARBAMATE COMPOUNDS

FIELD OF THE INVENTION

This invention relates to a process for preparing carbamate compounds by reacting an N-alkylcarbamoyl sulfonate salt with an active hydrogen containing compound in the presence of a base.

BACKGROUND OF THE INVENTION

The biological activity of a wide variety of N-alkyl carbamate compounds is well known. N-methyl carbamate compounds exhibit outstanding insecticidal activity. Among the more important N-methyl carbamate insecticides are aldicarb, carbaryl methomyl, carbofuran, landrin, and the like.

The most common conventional process for producing these compounds is by the reaction of an N-alkyl isocyanate with the appropriate active hydrogen containing compound. Many of these isocyanate reactants are highly reactive, resulting in syntheses with high product yields. However, the reactive nature of these compounds, particularly with water, often necessitates special precautions in their transportation, storage, and handling.

The Aldicarb synthesis process is illustrative. Aldicarb can be prepared by reacting methyl isocyanate (MIC) with 2-methyl-2-(methylthio) propionaldehyde oxime. Using this process, good yields are attainable in large scale production of this pesticide. However, special care must be exercised in transporting and sorting MIC, and in handling it.

This invention is directed to a process for preparing N-alkyl carbamate compounds without the use of N-alkyl isocyanate reactants. The sulfonate salts used as reactants in this process are stable solids and can be transported and stored without exercising special precautions. Another advantage is that the sulfonate salts are water soluble and the reactions in accordance with the present invention can be conducted using a water solvent.

SUMMARY OF THE INVENTION

The novel process for preparing a compound of the formula:

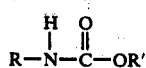

is carried out by reacting an active hydrogen containing compound containing an organic radical(R'), in the presence of a base, with a salt of the formula:

wherein:

R is a $C_1$-$C_8$ alkyl or phenyl group;
M+ is an alkali metal or ammonium ion, and
R' is an organic radical.

The process of this invention can be employed to produce any compound capable of being formed by the reaction of a lower alkyl isocyanate and an active hydrogen containing compound.

DESCRIPTION OF THE PREFERRED EMBODIMENTS

Illustrative of the above process are the following reactions in which R and M are as defined above and R' is an organic radical:

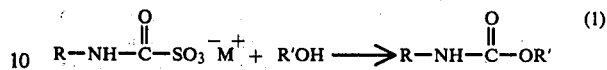

wherein R'OH can be, for example, (a) an aliphatic alcohol such as ethanol, 1-undecanol, methoxymethanol or methylthioethanol;
(b) an aromatic aliphatic alcohol such as benzyl alcohol and 3,4 dichlorobenzyl alcohol;
(c) a phenolic compound such as phenol, αnaphthol, dihydrobenzofuranol, benzothrophene-4-ol, tetrahydronaphthol, and benzodioxalanyl-4-ol;
(d) an oxime compound such as acetaldoxime, butyraldoxime, cyclododecanone oxime, 2-oxmino-1,4-dithiane, 2-methyl-2-methylthiopropionaldoxime, and 1-methylthioacetaldoxime.

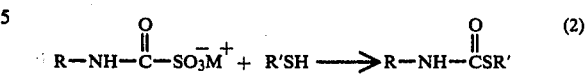

wherein RSH is a thiol compound such as methylmercaptan, ethylmercaptan, thiophenol and thionaphthol.

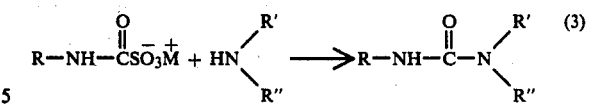

wherein R" is H or alkyl.

(a) a primary amine, such as methylamine or ethylamine; or
(b) a secondary amine, such as dimethylamine or methylethylamine.

It is understood that the active hydrogen containing compounds used as reactants in this process must contain at least one substituted or unsubstituted organic radical and may be further substituted with one or more substituents such as alkyl, chloro, fluoro, bromo, nitro, cyano, haloalkyl, alkoxy, alkylthio, diallylamino, alkanoyl and the like. Also, the alkyl or phenyl group R may be substituted with one or more of the above substituents.

The molar ratio of active-hydrogen containing compound to sulfonate salt reactants can vary over a wide range e.g., a molar ratio of 9:1 or higher to 1:9 or lower, although the preferred ratio is 1:1.

This reaction may be conducted in the presence or absence of a solvent depending upon the physical state of the reactants. The preferred solvent is water. This is in contrast to the prior art processes using MIC as a reactant, in which water may not be used as a solvent. This process may also be conducted in a mixture of water and organic solvents, or organic solvent alone that are inert to the reactants. Examples of the organic solvents useful in these mixtures include toluene, methylene chloride and chloroform.

A base is generally used as an acid acceptor in the present invention. The base can be either an organic or inorganic base. Illustrative of the inorganic bases which can be used are alkali metal hydroxides such as sodium hydroxide or potassium hydroxide. Illustrative of the organic bases suitable as acid acceptors are tertiary amines, such as triethylamine, pyridine, trimethylamine or 1,4-diazobicyclo-[2,2,2]-octane. An inorganic solvent is preferred. A preferred acid acceptor is sodium hydroxide.

When an inorganic base is used in a heterogeneous system, a phase transfer catalyst such as quaternary ammonium halides or crown ether compounds may optionally be used to facilitate the transfer of the reactants across the phase interface.

This reaction is neither temperature nor pressure sensitive and can be conducted over a broad range of temperatures and pressures to yield the desired products. This reaction is generally conducted at a temperature of from about 0° to about 100° C., preferably from about 20° C. to about 40° C. The reaction may be conducted at pressures that are superatmospheric, atmospheric; or subatmospheric. For convenience, these reactions are preferably conducted at room temperature and atmospheric or autogeneous pressure.

The N-alkylcarbamoyl sulfonate salt compounds used in this invention can be prepared by a variety of methods, as given in co-pending U.S. application Ser. No. 133,790 by the inventor herein, filed on an even date herewith. For example, an N-alkylisocyanate compound is reacted with the appropriate bisulfite salt to yield the desired product. These sulfonate compounds may also be prepared by reacting an N-alkylcarbamoyl halide compound with the appropriate metal bisulfite in the presence of an acid acceptor. For example, N-methylcarbannoyl chloride is reacted with sodium bisulfite in the presence of an acid acceptor to form sodium N-methylcarbamoyl sulfonate.

The following examples are intended to illustrate, but to in no way limit, the present invention.

Preparation of 1-Naphthyl-N-methylcarbamate

Examples I to VI illustrate the preparation of 1-naphthyl-N-methyl carbamate under various reaction conditions.

EXAMPLE I

A solution of sodium naphtholate, prepared by stirring 7.2 g (0.05 mole) of 1-naphthol and 2 g (0.05 mole) of sodium hydroxide in 50 ml of water, was added dropwise to a stirred solution of 9.0 g (0.056 mole) of sodium N-methylcarbamoylsulfonate in 50 ml of water in a 300 ml 4-necked flask. The addition was completed in approximately 20 minutes and the reaction temperature was kept at 21°-22° C. Stirring was continued for 2 hours at room temperature and then filtered to give 8.7 g of the crude product. A small amount of unreacted 1-naphthol was removed by washing with 30 ml of toluene. The desired product weighed 6.2 g (62°/° yield), and had a melting point of 139°-141° C.

EXAMPLE II

The reaction was carried out by adding a solution of 7.2 g (0.05 mole) of 1-naphthol and 2.0 g (0.05 mole) of sodium hydroxide in 50 ml of water to 8.1 g (0.05 mole) of sodium N-methylcarbamoylsulfonate in 50 ml of water at 20°-22°. The resulting reaction mixture was stirred for 1.5 hr and then filtered. The solid formed was washed with 50 ml of toluene to give 5.9 g (59°/° yield) of the desired product having a melting point of 139°-142° C.

EXAMPLE III

This reaction was carried out by the procedure outlined in Example II above using 10 g (0.062 mole) of sodium N-methylcarbamoylsulfonate, 7.2 g (0.05 mole) of 1-naphthol and 2.0 g (0.05 mole) of sodium hydroxide. After stirring for 3 hrs at room temperature and the same work-up as above gave 6.0 g (60°/° yield) of the desired product having a melting point of 140°-142° C.

EXAMPLE IV

In this example, a solution of 2.1 g (0.053 mole) of sodium hydroxide in 25 ml of water was added dropwise to a mixture of 9.0 g (0.056 mole) of sodium N-methylcarbamoylsulfonate and 7.2 g (0.05 mole) of 1-naphthol in 75 ml of water during a one hour period. The reaction mixture was stirred for 5 hours, filtered, and then washed with 5 ml of toluene to give 5.0 g (50°/° yield) of the desired product having a melting point of 141°-142° C.

EXAMPLE V

A mixture of 8.0 g (0.05 mole) of sodium N-methylcarbamoylsulfonate, 7.2 g (0.05 mole) of 1-naphthol, and 0.5 g (0.005 mole) of tetramethylammonium chloride in 50 ml of chloroform and 50 ml of water was stirred at room temperature. The reaction was monitered by TLC, and after 3 hrs there was no reaction. The mixture was refluxed for 24 hrs, and thin layer chromatigraphy showed the desired product had been produced.

EXAMPLE VI

The 25 ml of toluene was used as a co-solvent in this reaction. Using the procedure of Example II addition of 2.1 g (0.053 mole) of sodium hydroxide in 25 ml of water to a stirred solution of 1-naphthol (7.2 g 0.05 mole) and sodium N-methylcarbamoylsulfonate (9.0 g 0.056 mole) in 25 ml of toluene and 25 ml of water resulted in a formation of the desired product which was confirmed by thin layer chromatographic tests.

Preparation of 2-methyl-2 (methylthio) propionaldehyde 0-(methyl carbamoyl) oxime Example VII illustrates the preparation of 2-methyl-2(methylthio)propionaldehyde)-(methyl carbamoyl) oxime.

EXAMPLE VII

Into a solution of 6.7 g (0.05 mole) of 2-methyl-2-(methylthio) propionaldehyde oxime and 8.1 g (0.05 mole) of sodium N-methylcarbamoylsulfonate in 50 ml of water in a 250 ml 4-neck flask was added in dropwise fashion in sodium hydroxide solution (2.0 g (0.05 mole) in 10 ml of water). This solution was added during a five minute period at a temperature of 20°-25° C. The reaction mixture was stirred for 2 more hours at room temperature and then filtered to give 7.7 g of the desired product (yield, 87°/°) having a melting point of 98°-101° C.

Preparation of methyl N-[(Methyl-(carbamoyl)oxy] thioacetimidate

Example VIII illustrates the preparation of S-methyl N-[(methylcarbamoyl)oxy] thioacetimidate.

EXAMPLE VIII

The reaction was carried out by adding a solution of sodium hydroxide, 2.0 g (0.05 mole), in 10 ml of water to a stirred solution of 5.3 g (0.05 mole) of methomyl oxime and 8.1 g (0.05 mole) of sodium N-methylcarbamoylsulfonate in 20 ml of water. The addition at room temperature required 30 minutes.

The reaction mixture was further stirred at room temperature for 5 hours and then filtered to give 6.7 g of the desired product. Refiltration gave an additional 0.1 g of product. The yield of the combined product was 84°/°, and the melting point was 78°–81° C.

What is claimed is:

1. A process for preparing a compound of the formula:

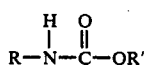

which comprises reacting a compound of the formula:

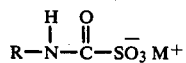

with an active hydrogen containing compound containing an organic radical, in the presence of a base, wherein:

M is an alkali metal or ammonium ion;

R is a $C_1$–$C_8$ alkyl or phenyl group; and,

R' is an organic radical from the active hydrogen containing compound, and wherein said active hydrogen containing compound is selected from the group consisting of an aliphatic alcohol, an aromatic aliphatic alcohol, a phenolic compound, a thiol compound, a secondary or primary amine, or an oxime.

2. A process according to claim 1 wherein said base is an alkali metal hydroxide.

3. A process according to claim 1 wherein said reaction is conducted in a solvent selected from the group consisting of water, toluene, methylene chloride, chloroform and mixtures thereof.

4. A process according to claim 3 wherein said solvent is water.

5. A process according to claim 1 wherein R' is a methyl group.

6. A process according to claim 1 wherein an alkali or ammonium salt of N-methylcarbamoyl sulfonate is reacted with 1-naphthol in the presence of an alkali base to prepare 1-naphthyl-N-methyl carbamate.

7. A process according to claim 1 wherein an alkali or ammonium salt of N-methylcarbamoylsulfonate is reacted with 2-methyl 2-(methylthio) propionaldehyde oxime in the presence of an alkali metal base to prepare 2-methyl-2(methylthio) propionaldehyde-)-(methyl carbamoyl) oxime.

8. A process according to claim 1 wherein an alkali or ammonium salt of N-methylcarbamoyl sulfonate is reacted with methomyl oxime in the presence of an alkali metal base to prepare methyl N-[(methylcarbamoyl)oxy] thioacetimidate.

* * * * *